US011523815B2

(12) United States Patent
Fu et al.

(10) Patent No.: US 11,523,815 B2
(45) Date of Patent: Dec. 13, 2022

(54) SIDE-LOADING KNOT CUTTER

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Rick Fu, Randolph, MA (US); Matthew D. Cunningham, Mansfield, MA (US); Allison Marie Stauffer, Brighton, MA (US)

(73) Assignees: Smith & Nephew, Inc., Memphis, TN (US); Smith & Nephew Orthopaedics AG, Zug (CH); Smith & Nephew Asia Pacific Pte. Limited, Singapore (SG)

( * ) Notice: Subject to any disclaimer, the term of this patent is extended or adjusted under 35 U.S.C. 154(b) by 392 days.

(21) Appl. No.: 16/900,327

(22) Filed: Jun. 12, 2020

(65) Prior Publication Data

US 2020/0390434 A1 Dec. 17, 2020

Related U.S. Application Data

(60) Provisional application No. 62/861,161, filed on Jun. 13, 2019.

(51) Int. Cl.
*A61B 17/04* (2006.01)
*A61B 17/00* (2006.01)

(52) U.S. Cl.
CPC ...... *A61B 17/0467* (2013.01); *A61B 17/0469* (2013.01); *A61B 2017/00353* (2013.01); *A61B 2017/00393* (2013.01); *A61B 2017/0474* (2013.01); *A61B 2017/0475* (2013.01)

(58) Field of Classification Search
CPC ............ A61B 17/0467; A61B 17/0469; A61B 2017/00353; A61B 2017/00393; A61B 2017/0474
See application file for complete search history.

(56) References Cited

U.S. PATENT DOCUMENTS

| | | | |
|---|---|---|---|
| 7,879,055 B1 * | 2/2011 | Stone ................. | A61B 17/0467 606/170 |
| 8,211,123 B2 * | 7/2012 | Gross ................. | A61B 17/0469 606/167 |
| 8,834,497 B2 * | 9/2014 | Snell .................. | A61B 17/0467 606/167 |
| 8,911,457 B2 * | 12/2014 | Koogle, Jr. ........ | A61B 17/0469 606/148 |
| 9,247,935 B2 * | 2/2016 | George .............. | A61B 17/0469 |
| 10,426,462 B2 * | 10/2019 | Haberman .......... | A61B 17/0467 |
| 10,595,854 B2 * | 3/2020 | Nachmias .......... | A61B 17/0467 |

(Continued)

*Primary Examiner* — Phong Son H Dang
(74) *Attorney, Agent, or Firm* — Norman F. Hainer, Jr.

(57) ABSTRACT

A knot pushing and suture-cutting device is disclosed including a handle having a multi-positional control and an inner shaft and outer tube extending from the handle. The inner shaft and outer tube both comprise slots and the outer tube is both axially and rotationally moveable relative to the inner shaft, to move the inner shaft and outer tube slots relative to each other. In a first configuration, the inner shaft and outer tube slots are aligned and configured to receive a suture therein. In a second configuration, the slots are configured to lock the suture within a lumen of the inner shaft. In a third configuration a cutting edge on the outer slot is configured to cut the suture.

16 Claims, 7 Drawing Sheets

(56) References Cited

U.S. PATENT DOCUMENTS

| | | | |
|---|---|---|---|
| 11,219,447 B2* | 1/2022 | Juan | A61B 17/0467 |
| 11,284,878 B2* | 3/2022 | Harrison | A61B 17/0467 |
| 11,401,964 B2* | 8/2022 | Held | F16B 21/125 |
| 2007/0005081 A1* | 1/2007 | Findlay, III | A61B 17/0487 |
| | | | 606/148 |
| 2007/0173865 A1* | 7/2007 | Oren | A61B 17/0467 |
| | | | 606/148 |
| 2007/0213746 A1 | 9/2007 | Hahn et al. | |
| 2008/0234729 A1* | 9/2008 | Page | A61B 17/0485 |
| | | | 606/232 |
| 2009/0228026 A1 | 9/2009 | Koogle, Jr. et al. | |
| 2014/0005689 A1* | 1/2014 | Griffiths | A61B 17/0467 |
| | | | 606/138 |
| 2015/0088163 A1* | 3/2015 | George | A61B 17/0467 |
| | | | 606/138 |
| 2018/0228485 A1 | 8/2018 | Haberman et al. | |
| 2018/0235600 A1 | 8/2018 | Nachmias et al. | |
| 2022/0257096 A1* | 8/2022 | Weitzner | A61B 1/00165 |

\* cited by examiner

SIDE-LOADING KNOT CUTTER

CROSS-REFERENCE TO RELATED APPLICATIONS

This application claims priority to and benefit of U.S. Provisional Application No. 62/861,161 filed Jun. 13, 2019 entitled "SIDE-LOADING KNOT CUTTER", the contents of which are incorporated herein by reference in their entirety for all purposes.

FIELD OF THE INVENTION

The present invention relates to suturing techniques, devices and methods, and in particular, to a combination knot pusher and suture cutter apparatus and method of use during surgery, such as arthroscopic surgery.

BACKGROUND

Suturing of tissue during surgical procedures is time consuming and can be particularly challenging in difficult to access body regions and regions that have limited clearance, such as regions partially surrounded or covered by bone. Suturing instruments have been developed to assist in accessing and treating internal body regions, and to generally assist a physician in repairing tissue. Although many such devices are available for endoscopic, arthroscopic, and/or percutaneous use, these devices suffer from a variety of problems, including limited ability to navigate and be operated within the tight confines of the body, risk of injury to adjacent structures, problems controlling the position and/or condition of the tissue before, during, and after passing the suture, as well as problems with the reliable functioning of the suture passer.

Further, when performing surgery, such as arthroscopic surgery, suture knot placement can be an important yet difficult step. Suture knot placement devices tend to have closed loop distal ends and/or smaller apertures that the suture must be threaded through. This may require a second suture-threading tool and thereby a more complicated surgical process. Any failed attempts at threading the suture may result in destruction or deformation of the stiffened suture end increasing difficulty of use. Additionally a suture-threader may be included as a one-time use device for placing the suture and/knot within the cutter tool, adding cost should multiple sutures require placement. Additionally, after the knots are tied, surgeons will generally trim excess tails of the suture so that only the necessary amount of suture remains at the repair site. Some attempted solutions may have an open-loop end configuration that may be easier to load the suture therein. These devices however do not sufficiently address the needs of the surgeon as they allow the suture to migrate out of the device during knot reduction, or alternatively increase complexity of use and additional components to manage suture migration. They are also insufficient in that they do not provide a suture reloading option without the need for a second tool, or complex use that may increase steps and procedure time.

Described herein are apparatuses for pushing a knot of suture and cutting the suture that may address the problems and needs identified above.

NOTATION AND NOMENCLATURE

Certain terms are used throughout the following description and claims to refer to particular system components. As one skilled in the art will appreciate, companies that design and manufacture electrosurgical systems may refer to a component by different names. This document does not intend to distinguish between components that differ in name but not function.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

Reference to a singular item includes the possibility that there are plural of the same items present. More specifically, as used herein and in the appended claims, the singular forms "a," "an," "said" and "the" include plural references unless the context clearly dictates otherwise. It is further noted that the claims may be drafted to exclude any optional element. As such, this statement serves as antecedent basis for use of such exclusive terminology as "solely," "only" and the like in connection with the recitation of claim elements, or use of a "negative" limitation. Lastly, it is to be appreciated that unless defined otherwise, all technical and scientific terms used herein have the same meaning as commonly understood by one of ordinary skill in the art to which this invention belongs.

Where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

BRIEF DESCRIPTION OF THE DRAWINGS

For a detailed description of example embodiments, reference will now be made to the accompanying drawings in which.

SUMMARY

Figure 1:
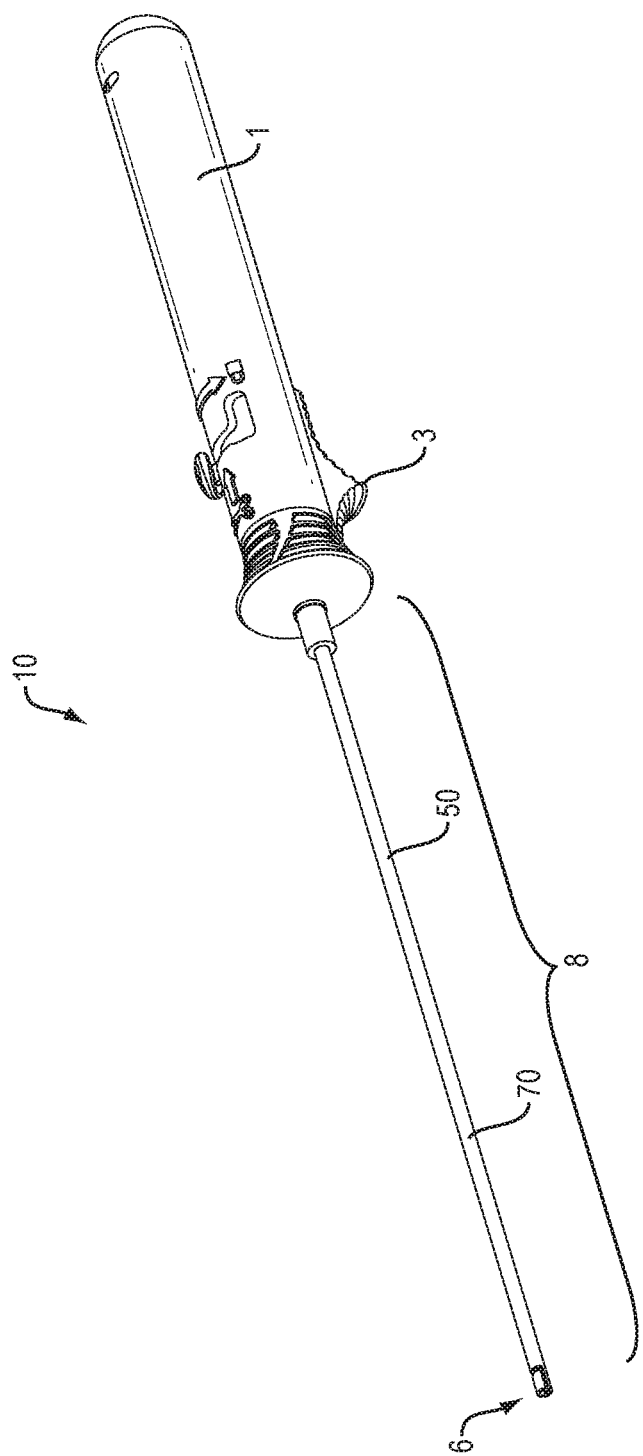
FIG. 1 illustrates an isometric view depicting a combination side loading knot pusher and suture cutting instrument in accordance with at least one embodiment disclosed.

Generally this disclosure describes an instrument for side-loading a length of suture, securing the length of suture and thereafter cutting or trimming the length of suture. The specification now turns to an example instrument.

Various non-limiting embodiments are directed to a combination knot pushing and suture-cutting device including a handle with an inner shaft and outer tube extending therefrom. The outer tube is axially and rotationally moveable relative to the inner shaft. The inner shaft may define a tube. Both the inner shaft and outer tube includes a slot configured to receive a suture therein. The outer slot also includes a cutting edge. The handle includes a locking member on the handle operatively connected to the outer tube, the locking member configured to rotate the outer tube relative to the inner tube from a first position, wherein the inner shaft slot and outer tube slots are aligned so as to allow side loading of the suture into the slots; to a second position, wherein the inner and outer slots are not aligned, thereby locking the suture within the inner tube. An actuator on the handle is operatively connected to the outer tube for axially moving the outer tube relative to the inner tube for shearing the suture between the inner tube and the cutting edge.

The inner shaft may have a distal-most surface with an opening in communication with the inner slot, the opening configured to allow a suture therethrough and prevent a knot portion of said suture therethough. The outer tube may be operatively coupled to a biasing member disposed within the handle to urge the outer tube distally. In the first position a distal-most end of both the inner shaft and outer tube may be axially aligned. The locking member and actuator may be the same control and wherein moving this control in a first direction rotates the outer tube and moving this control in a second direction axially translates the outer tube. The control and/or locking member and/or actuator may be located on the handle to be easily or readily thumb actuated.

In a further example embodiment a knot pushing and suture-cutting device is disclosed including a handle and inner and outer tubes extending from the handle. The outer tube is axially and rotationally moveable relative to the inner tube. The inner tube includes a slot and the outer tube includes a slot and a cutting edge along an edge of said slot. The inner and outer tubes are coaxially disposed relative to each other and slide relative to each other between a first, second and third position. In the first position, the inner and outer slots are oriented to provide a side-loading passage for a length of suture therethrough, and into a lumen of the inner tube. In the second position, a side-loading portion of the outer slot is angularly offset from the side-loading portion of the inner slot to retain the length of the suture within the inner slot lumen. In the third position, the outer slot is both angularly and axially offset from the inner slot to retain and cut the length of suture. The handle may comprise an actuator operatively connected to the outer tube, the actuator configured to rotate the outer tube relative to the inner tube from the first position to the second position. The actuator may also be configured to axially move the outer tube relative to the inner tube for shearing the suture with the cutting edge. The inner tube distal-most surface may define an opening in communication with the inner lumen, the opening configured to allow a suture therethrough and prevent a knot portion of said suture therethough. The distal-most surface may provide a pushing surface for the knot. The outer tube may be operatively coupled to a biasing member disposed within the handle to urge the outer tube distally. In the first position a distal-most end of both the inner and outer tube are axially aligned. The actuator may be moved in a first direction to rotate the outer tube and in a second direction that is different to the first direction to axially translate the outer tube.

A method of using a knot pushing and suture-cutting tool may include the steps of: side-loading a length of suture through a lateral slot of an outer sleeve and a lateral slot of inner tube and into and along a lumen of the inner tube disposed at a distal end of a surgical instrument; rotating the lateral slot of the outer tube away from the lateral slot of the inner tube so as to cover the inner tube lateral slot and lock the length of suture within the inner lumen; drawing the length of suture proximally so as to engage a knot of the suture against a distal surface of the inner tube; and retracting the outer tube relative to the inner tube so as to cut the length of suture with a cutting edge of the outer tube. The outer tube may be operatively coupled to a handle and an actuator of said handle, and the step of rotating may be performed by moving the actuator in a first direction and the step of retracting may be performed by moving the actuator in a different direction. After retracting the outer slot, release of the actuator may return the outer slot to a less retracted configuration. The handle may comprise a biasing element configured to urge the outer slot to a less retracted configuration. The inner tube slot may include a proximal surface configured to guide the length of suture towards the cutting edge while retracting the outer tube relative to the inner tube to cut the length of suture with a cutting edge of the outer tube.

DETAILED DESCRIPTION

The following discussion is directed to various embodiments. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

The disclosure may generally include a device that both engages a knot associated with a suture and thereafter cuts the suture. The device is operable to side load a suture within the device distal end and may have an "L" or "S" side slot at its distal end to receive the suture therein. The device may include two concentric tubes that move relative to each other to retain the suture, reduce the knot and also cut the suture, depend on the relative locations of the two tubes. Accordingly, the side-loading knot pusher and suture cutter may improve the efficiency of a surgeon using the instrument, and may reduce fatigue induced by tedious processes such as attempting to thread a suture.

Referring now to FIG. 1, an exemplary embodiment is shown of a side-loading knot pusher and suture cutter, hereafter referred to simply as "instrument" 10. In this example, the instrument 10 includes handle 1 and shaft 8. For purposes of discussion, it is considered that the handle 1 is proximal, while the shaft is distal. Generally, such orientation is consistent with how the instrument 10 will be deployed during surgery. However, terms of geometry are not to be construed as limiting of the teachings herein.

Associated with handle 1 is at least one control 3. Generally, the control 3 provides for manipulation of a cutting sleeve 50. The cutting sleeve 50 is an outer sleeve or tubular member coaxially disposed around an inner shaft 70, inner shaft operable as "knot pusher". Together, knot pusher 70 and cutting sleeve 50 form the shaft 8. Design of the side-loading distal end 6 is such that a surgeon may quickly and efficiently capture suture and secure a knot that is disposed within the suture.

As discussed herein, the suture may include a slipknot. However, this is not limiting of the teachings herein. For example, the suture may include a one-way slidable knot, an adjustable knot, or any other kind of knot deemed appropriate. Generally, the nature of the knot is to be judged by the user (e.g., a surgeon) or another similarly situated party.

Beginning with the distal end 6, shown in more detail in FIGS. 2A-2F, details of, and the steps of operation of cutting sleeve 50 and knot pusher 70 can be seen. Sleeve 50 defines a lumen for receiving a portion of knot pusher 70. Knot pusher 70 may be in the form of an elongate shaft with a lumen through at least a distal portion of shaft. In some embodiments knot pusher 70 may be in the form of an elongate tube. Outer sleeve 50 further comprises a slot 54 through the entire wall thickness of the tube 50 that may be in a shape of and "L" "J" or "S". Slot 54 extends up to and including a distal-most end 52 of sleeve 50. Slot 54 defines a first slot portion 54A extending axially from the distal most end 52. Slot 54 defines a second slot portion 54B that extends circumferentially further around outer tube 50 than the first slot portion 54A. Stated otherwise, second slot portion 54B extends approximately perpendicularly relative to a longitudinal axis of sleeve 50. Second slot portion 54B further comprises a cutting edge 58. Cutting edge 58 is circumferentially spaced from first slot portion 54A to inhibit inadvertent suture cutting while side loading suture 100. First elongate slot portion 54A has a circumferential width "X" sufficient to receive a suture therethough. Best seen in FIGS. 2B, 2E and 2F, second slot portion 54B has a tapered axial opening Y, configured to direct a length of suture towards the cutting edge 58 for improved cutting reliability. Inner shaft 70 is coaxially disposed within outer tube 50 and defines a lumen 72 therethrough for receiving a length of suture. Inner tube 70 further comprises a slot 74 through the wall thickness of the tube 70 that may be shaped in a "L", "J" or "S" shape that approximates at least portions of the shape of the slot 54 in the outer tube 50. The inner shaft 70 provides the primary knot pushing surface 71 as well as houses the suture within lumen 72 during use. Slot 74 extends up to and including a distal-most end of inner tube 70, and includes a first slot portion 74A and second portion 74B. First slot portion 74A axially extends in a proximal direction from distal-most inner shaft end, similar to first slot portion 54A. Second slot portion 74B extends circumferentially therefrom and may or may not comprise a cutting edge.

Figure 2A:
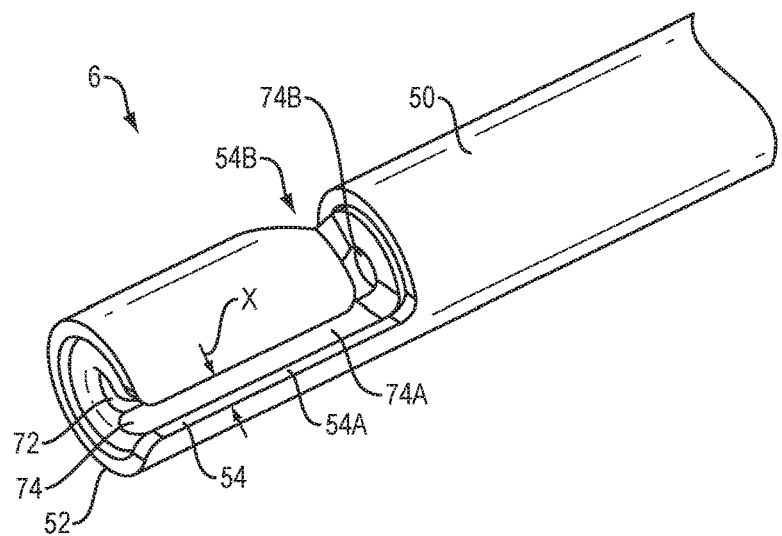
FIG. 2A illustrates an isometric view of a distal end of a combination side loading knot pusher and suture cutting instrument in an unlocked position, in accordance with at least one embodiment disclosed.
Figure 2B:
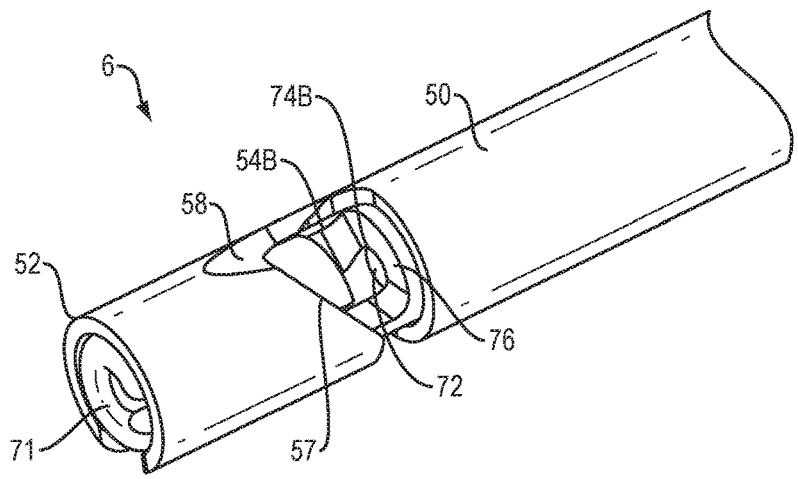
FIG. 2B illustrates an isometric view of a distal end of a combination side loading knot pusher and suture cutting instrument in a locked position, in accordance with at least one embodiment disclosed.
Figure 2C:
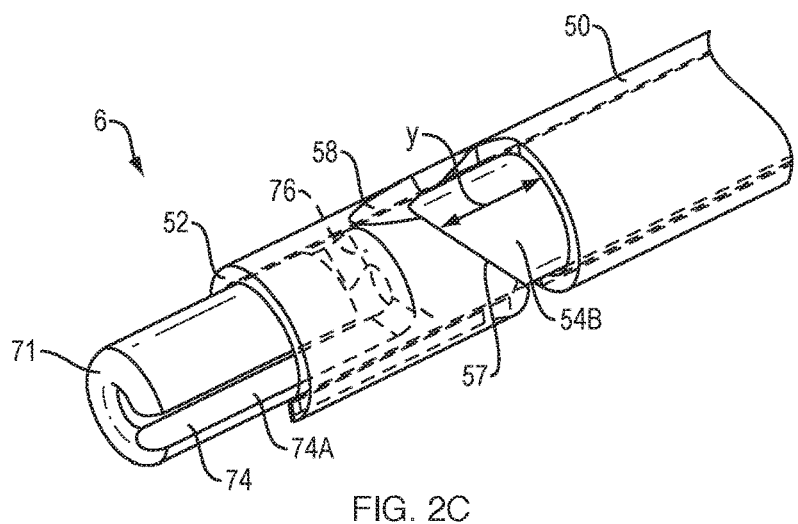
FIG. 2C illustrates an isometric view of a distal end of a combination side loading knot pusher and suture cutting instrument in a cut position, in accordance with at least one embodiment disclosed.
Figure 2D:
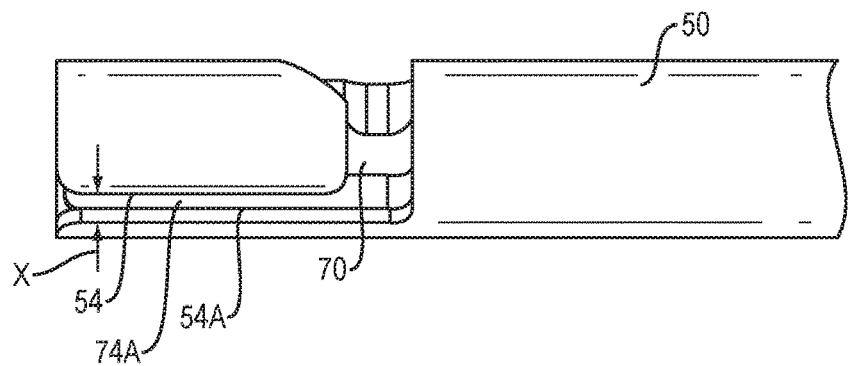
FIG. 2D illustrates a top view of FIG. 2A, in accordance with at least one embodiment disclosed.
Figure 2E:
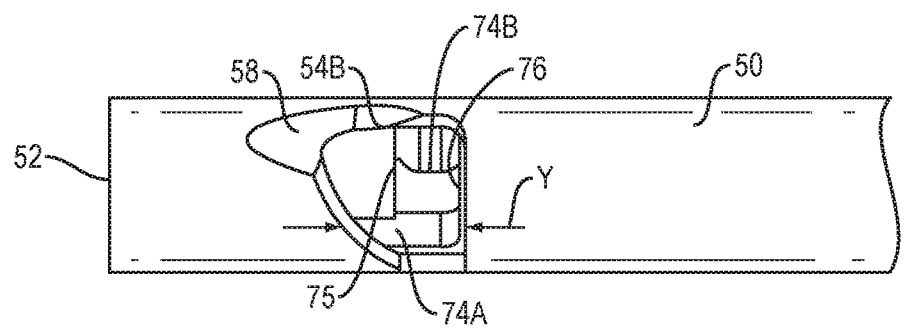
FIG. 2E illustrates a top view of FIG. 2B, in accordance with at least one embodiment disclosed.
Figure 5A:
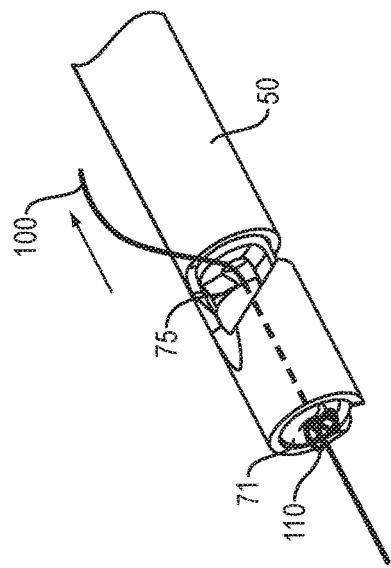
FIGS. 5A-5D illustrate a method of using a combination side loading knot pusher and suture-cutting instrument, in accordance with at least one embodiment disclosed.
Figure 5B:
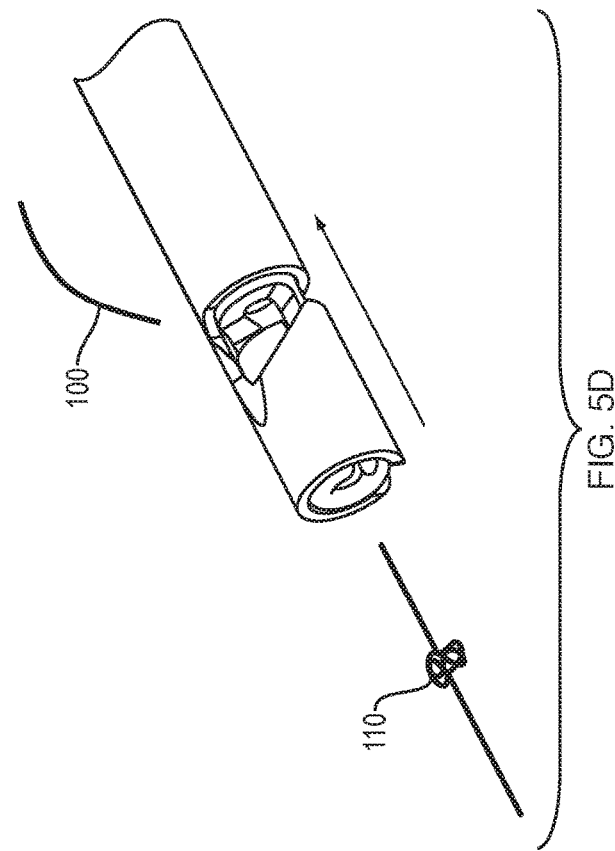

FIGS. 2A, 2D and 5A shows an open configuration, wherein the inner shaft 70 and outer sleeve 70 are both axially aligned with each other and oriented such that first slot portions 54A and 74A both approximately align, to allow suture 100 to be inserted through both slots 54A and 74A and into and along the inner shaft lumen 72. A side slot opening as shown in FIGS. 2A, 2D and 5A facilitates easy insertion of suture both inside the patient and outside. Suture 100 preferably includes a knot 110 (FIG. 5A-5D). Suture 100 may include a plurality of lengths of suture. FIGS. 2B, 2E and 5B shows the instrument 10 in a second configuration, or locked/closed configuration. The outer sleeve 70 has been axially rotated relative to the inner shaft 50 so that the relative slot portions (54A and 74A) no longer align and the suture 100 is enclosed within inner lumen 72. Stated otherwise, outer tube 50 covers a sufficient extent of the inner shaft first slot portion 74A to prevent suture 100 from migrating laterally out of distal end 6 through the slots 54 and 74. In addition, inner shaft second portion 74B is shaped to retain length of suture away from cutting edge 58. Stated otherwise, in the second position a circumferential extending edge of inner tube 75, that may define a boundary of the second slot portion 74B, aligns with a proximal-most edge of cutting edge 58 to protect suture from being inadvertently cut while the device is in the second configuration. In this second configuration, the knot 110 may be drawn up against distal-most end 71 of inner shaft. Inner shaft lumen 72 is therefore configured to have a diameter that receives and allows at least one length of suture 100 to slide therethrough and yet sufficiently smaller than a cross sectional dimension of knot 110 to provide a surface for knot 110 to be drawn up against, and not drawn significantly into the lumen 71. Exemplary suture sizes may include USP size 0, #2-0, and #3-0. Exemplary lumen diameters of inner tube may include Ø0.016-Ø0.024 inches.

Figure 2F:
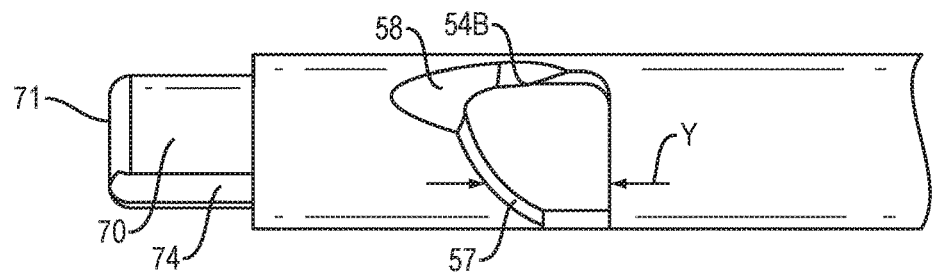
FIG. 2F illustrates a top view of FIG. 2C, in accordance with at least one embodiment disclosed.
Figure 5C:
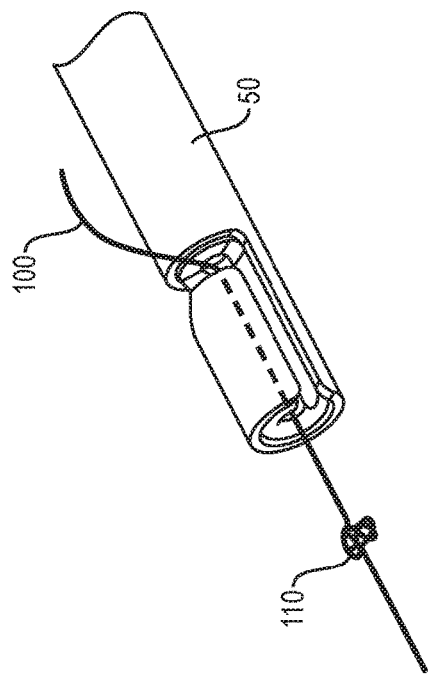
Figure 5D:
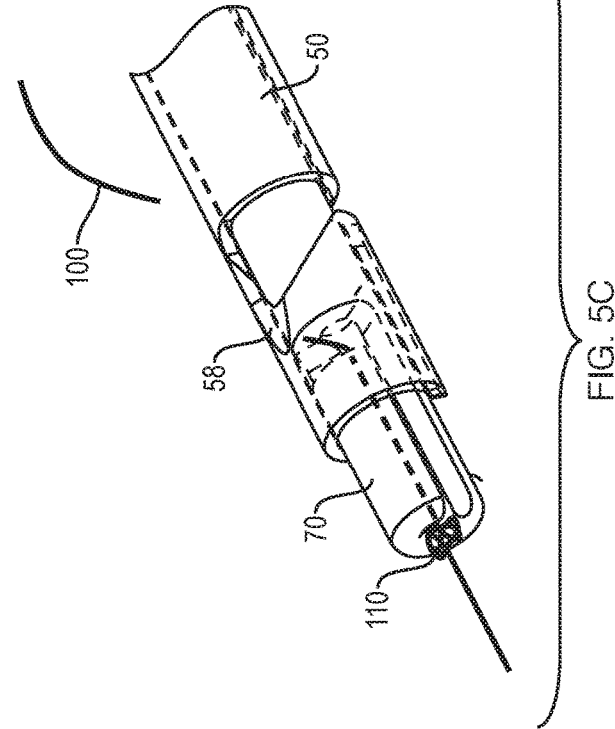

FIGS. 2C, 2F and 5C shows instrument in a cutting configuration, wherein the outer and inner tube 50 and 70 respectively move axially relative to each other. Outer sleeve 50 may be retracted while the inner tube remains stationary. As outer sleeve 50 retracts, suture 100 is pushed against cutting edge 58 to trim suture end(s). Cutting edge 58 is disposed long a distal corner/edge of second slot portion 54B. As outer sleeve 50 retracts, surface 76 at proximal end of inner shaft slot 74 may cooperate with angled surface 57 of outer slot to guide suture 100 towards the distal corner to reliably trim suture end. Sharp cutting edge 58 facilitates cutting of the suture tail by means of shearing between it and the inner tube surface 76. Explained in more detail later, outer sleeve 50 may be spring loaded to spring back to the second or locked configuration once an actuator in the handle 1 is released—as shown in FIG. 5D. Instrument 10 may then be withdrawn from knot 110 (FIG. 5D).

Figure 3A:
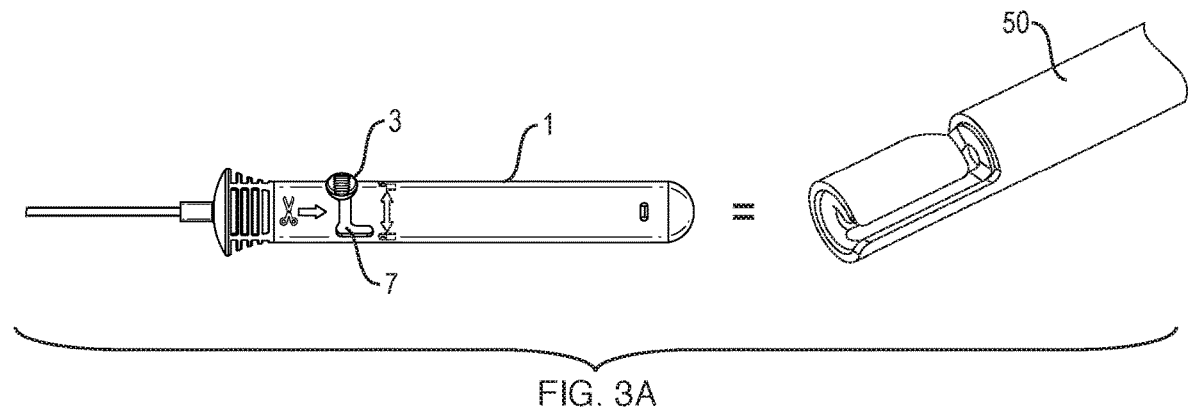
FIGS. 3A, 3B and 3C, illustrates three relative control positions on a handle of a combination side loading knot pusher and suture cutting instrument, in accordance with at least one embodiment disclosed.
Figure 3B:
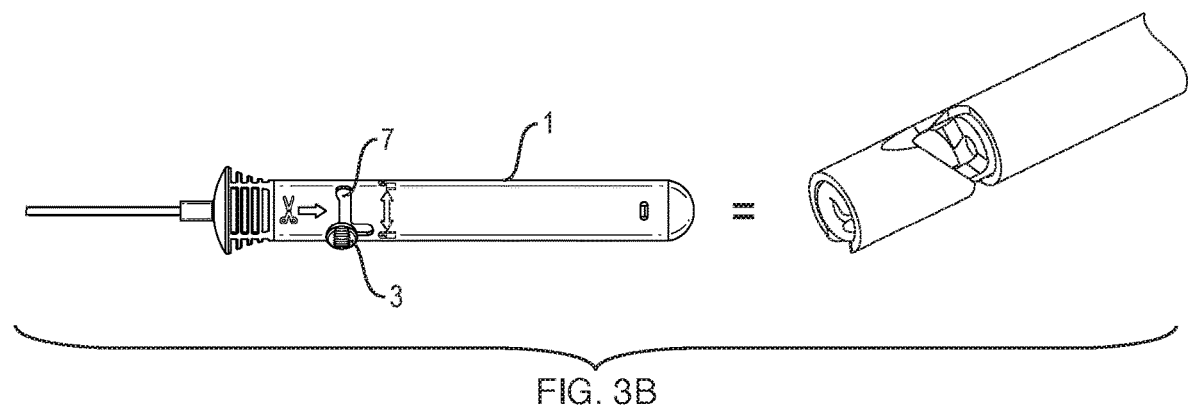
Figure 3C:
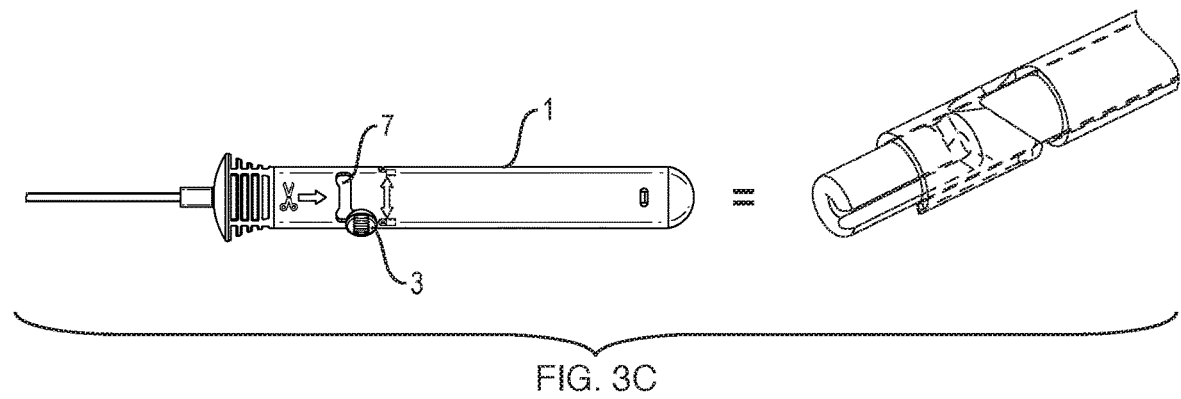

FIGS. 3A-3C show the handle 1 with actuator 3 in three positions corresponding with distal end configurations as described in FIGS. 2A-2C. Handle 1 may include a multi-position gated slot 7 to allow movement of thumb actuator control 3 both around and axially along handle 1. Alternatively, instrument 10 may include a first control to move outer sleeve 50 between first and second position, and a second separate control to actuate cutting. Actuator or control 3 may be operably coupled to outer tube 50 and controls position of outer tube 50 relative to stationary inner shaft 70. Inner shaft may be fixedly coupled to handle 1. In FIG. 3A control 3 is in a first position that orients outer sleeve slot 74 in alignment with inner tube slot 74 as shown in FIG. 2A and FIG. 5A and reproduced beside FIG. 3A for convenience. Moving control 3 to a second position as shown in FIG. 3B, rotates the outer sleeve 50 to the second or locked configuration as shown in FIGS. 2B and 5B and reproduced beside FIG. 3A for convenience. Axially retracting control 3 to position as shown in FIG. 3C, retracts outer sleeve 50 to trim suture. In alternative embodiments control 3 may be axially advanced to cut suture.

Figure 4:
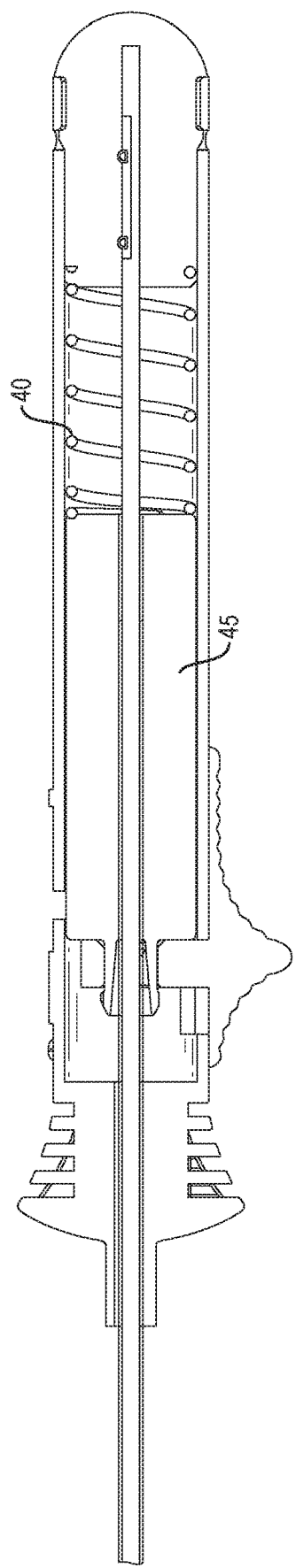
FIG. 4 schematically shows a cross-section view of a side loading knot pusher and suture cutting handle.

Seen in FIG. 4, inside the handle 1 is a spring or biasing element 40 that urges a shuttle 45 connected to the outer sleeve 50. This shuttle 45 can translate axially and rotate within the handle housing. Control 3 is configured to be operated by a thumb while the rest of the user's hand may hold the instrument 10. Control 3 is operably coupled to the shuttle 45 through multi-position-gated-slot 7 in the handle, limiting its translation and rotation. Biasing element 40 is configured to urge the control 3 and also outer sleeve 50 back to the second position after control 3 has retracted the outer tube 50 and trimmed the suture tail. This will aid in releasing the suture and knot from the instrument and withdrawal of the instrument from the target site hereafter releasing the suture with the knot from the instrument 10.

Figure 6A:
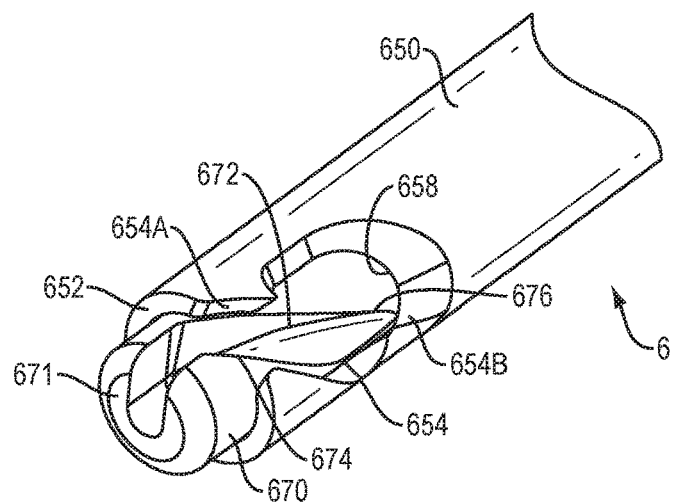
FIG. 6A illustrates an isometric view of a distal end of a combination side loading knot pusher and suture cutting instrument in an unlocked position, in accordance with at least one embodiment disclosed.
Figure 6B:
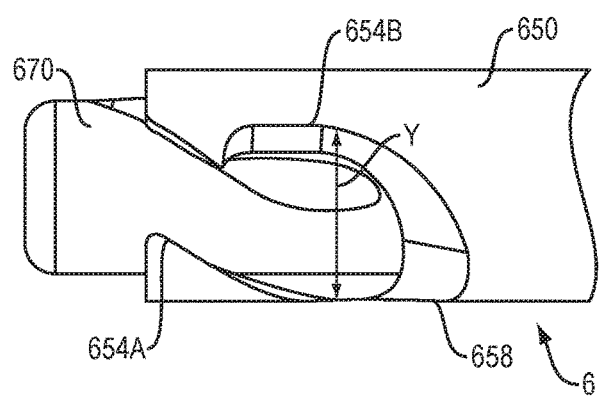
FIG. 6B illustrates a top view of a distal end of a combination side loading knot pusher and suture cutting instrument in a locked position, in accordance with at least one embodiment disclosed.
Figure 6C:
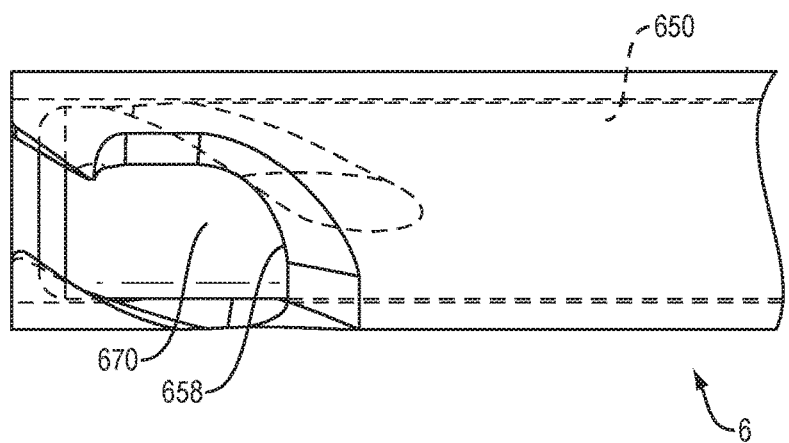
FIG. 6C illustrates a top view of a distal end of a combination side loading knot pusher and suture cutting instrument in a cut position, in accordance with at least one embodiment disclosed.

FIGS. 6A, 6B and 6C show an alternative embodiment of distal end 6, including a cutting sleeve 650 and knot pusher 670. Sleeve 650 defines a lumen for receiving a portion of knot pusher 670. Sleeve 650 further comprises a slot 654 through the entire wall thickness of the sleeve 650. Slot 654 extends up to and including a distal-most end 652 of sleeve 650. Slot 654 defines a distal slot portion 654A extending axially from the distal most end 652. Slot 654 defines a proximal slot portion 654B that extends circumferentially further around outer tube 650 than the distal slot portion 654A. Proximal slot portion 654B further comprises a cutting edge 658. Cutting edge 658 defines a proximal most edge of slot 654 and is proximally spaced from a proximal most edge 676 of inner shaft channel 674 to inhibit inadvertent suture cutting while side loading the suture (suture not shown in this embodiments). Distal slot portion 654A has a circumferential width "X" sufficient to receive a suture therethough. Knot pusher 670 defines an inner shaft coaxially disposed within outer tube 650 and defines a helical or angled channel 672 for receiving a length of suture therein. Knot pusher channel 672 defines a lateral elongate suture receiving opening 674 that approximates at least portions of the shape of the distal slot portion 654A in the outer tube 650. The knot pusher 670 provides the primary knot pushing surface 671 as well as houses the suture within channel 672 during use. Channel 672 extends up to and including a distal-most end of knot pusher 670. Having an angled or helically formed suture receiving channel 672 may make insertion of the suture easier than the embodiment disclosed in at least FIG. 2A-2F. The suture may be inserted at an angle to the knot pusher longitudinal axis in this embodiment. In the previously disclosed embodiment, the suture may need to be placed both substantially parallel to the longitudinal axis and also pushed radially into the knot pusher channel 672. Knot pusher channel 672 defines a proximal edge 676 that is spaced away from the cutting edge 658 while placing and locking the suture.

FIG. 6A shows an open configuration, wherein the knot pusher 670 and outer sleeve 650 are oriented such that distal slot portion 654A and knot pusher opening 674 both approximately align, to allow a suture to be inserted therethrough and into and along the knot pusher channel 672. A side slot opening as shown in FIG. 6A facilitates easy insertion of suture both inside the patient and outside. Suture 100 preferably includes a knot 110 (shown in FIG. 5A-5D). Suture 100 may include a plurality of lengths of suture. FIG. 6B shows the distal end 6 in a second configuration, or locked/closed configuration. The outer sleeve 670 has been axially rotated relative to the knot pusher 650 so that the relative slot and opening portions (554A and 674) no longer align and the suture 100 is enclosed within channel 672. Stated otherwise, outer tube 650 covers a sufficient extent of the knot pusher channel 672 to prevent suture 100 from migrating laterally out of distal end 6 through the slot 654 and opening 674. In addition, knot pusher proximal most edge 676 is shaped to retain length of suture away from cutting edge 658. In this second configuration, the knot 110 may be drawn up against distal-most end 671 of knot pusher. Channel 672 is therefore configured to have a distal-most opening that receives and allows at least one length of suture 100 to slide therethrough and yet sufficiently smaller than a cross sectional dimension of knot 110 to provide a surface for knot 110 to be drawn up against, and not drawn significantly into the channel 671. Exemplary suture sizes may include USP size 0, #2-0, and #3-0. Exemplary channel cross sections of inner shaft may include Ø0.016-Ø0.024 inches.

FIG. 6C shows distal end 6 in a cut configuration, wherein the outer sleeve 650 and knot pusher 670 respectively move axially relative to each other. Outer sleeve 650 may be advanced while the inner tube remains stationary. As outer sleeve 650 advances, suture 100 is pushed against cutting edge 558 to trim suture end(s). Cutting edge 658 is disposed along a proximal edge of proximal slot portion 654B. Sharp cutting edge 658 facilitates cutting of the suture tail by means of shearing between it and the opening 674. Outer sleeve 650 may be spring loaded to spring back to the second or locked configuration once an actuator in the handle 1 is released. Instrument 10 may then be withdrawn from knot 110 (similar to shown in FIG. 5D).

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

The invention claimed is:

1. A knot pushing and suture-cutting device comprising:
a handle;
an inner shaft and outer tube extending from the handle, the outer tube axially and rotationally moveable relative to the inner shaft, the inner shaft comprising an inner slot and the outer tube comprising an outer slot, the inner and outer slots configured to receive a suture therein, the outer slot further comprising a cutting edge;
an actuator member on the handle operatively connected to the outer tube, the actuator member configured to rotate the outer tube from a first position, wherein the inner shaft and the outer slot are aligned, to a second position, wherein the inner shaft and the outer slot are not aligned, thereby locking the suture within the inner shaft; and wherein the actuator is also operatively connected to the outer tube for axially moving the outer tube relative to the inner tube for shearing the suture between the inner tube and the cutting edge.

2. The knot pushing and suture-cutting device of claim 1 wherein the inner shaft has a distal-most surface having an opening in communication with the inner slot, the opening configured to allow a suture therethrough and prevent a knot portion of said suture therethough.

3. The knot pushing and suture-cutting device of claim 1 wherein the outer tube is operatively coupled to a biasing member disposed within the handle to urge the outer tube distally.

4. The knot pushing and suture-cutting device of claim 1 wherein in the first position a distal-most end of both the inner shaft and outer tube are axially aligned.

5. The knot pushing and suture-cutting device of claim 1 wherein moving the actuating member in a first direction rotates the outer tube and moving the actuating member in a second direction axially translates the outer tube.

6. A knot pushing and suture-cutting device comprising:
a handle;
a knot pusher and outer tube extending from the handle, the outer tube axially and rotationally moveable relative to the inner shaft, the knot pusher comprising a slot and the outer tube comprising an outer slot and a cutting edge;
wherein the knot pusher and outer slot are configured to move between a first, second and third position relative to each other, wherein in the first position the knot pusher and outer slot are oriented to provide a side-loading passage for a length of suture therethrough and into a channel within the knot pusher;
wherein in the second position the outer slot is angularly offset from the knot pusher slot to retain the length of the suture therein;
wherein in the third position, the outer slot is both angularly and axially offset from the knot pusher slot and the length of suture is cut; wherein the handle comprises an actuator operatively connected to the outer tube, the actuator configured to rotate the outer tube relative to the knot pusher from the first position to the second position; and wherein the actuator is moved in a first direction to rotate the outer tube and in a second direction to axially translate the outer tube.

7. The knot pushing and suture-cutting device of claim 6 wherein the actuator is further configured to axially move a cutting edge of the outer slot relative to the knot pusher to shear the suture therebetween.

8. The knot pushing and suture-cutting device of claim 6 wherein the knot pusher has a distal-most surface having an opening in communication with the knot pusher slot, the channel configured to allow a suture therethrough and prevent a knot portion of said suture therethough.

9. The knot pushing and suture-cutting device of claim 6 wherein the outer tube is operatively coupled to a biasing member disposed within the handle to urge the outer tube distally.

10. The knot pushing and suture-cutting device of claim 6 wherein in the first position a distal-most end of both the knot pusher and outer tube are axially aligned.

11. The knot pushing and suture-cutting device of claim 6 wherein in the first and second position a proximal-most portion of the knot pusher slot is disposed axially adjacent the cutting edge to space the length of suture from the cutting edge.

12. A method of pushing a knot of a suture and thereafter trimming said suture comprising:
side-loading a length of suture through a slot of an outer sleeve and a slot of inner shaft and into and along a lumen of the inner shaft disposed at a distal end of an surgical instrument;
rotating the slot of the outer sleeve away from the slot of the inner shaft so as to cover the inner shaft slot and retain the length of suture within the inner shaft lumen;
drawing the length of suture proximally so as to abut a knot of the suture against a distal surface of the inner shaft; and
retracting the outer sleeve relative to the inner shaft so as to cut the length of suture with a cutting edge of the outer sleeve slot.

13. The method of claim 12 wherein the outer sleeve is operatively coupled to a handle and an actuator of said handle; and wherein the step of rotating is performed by moving the actuator in a first direction and the step of retracting is performed by moving the actuator in a different direction.

14. The method of claim 13 wherein after retracting the outer sleeve, release of the actuator returns the outer sleeve to a less retracted configuration.

15. A method of claim 14 wherein the handle comprises a biasing element configured to urge the outer sleeve to a less retracted configuration.

16. A method of claim 12 wherein the inner shaft slot has a proximal surface configured to guide the length of suture towards the cutting edge during the step of retracting the outer sleeve relative to the inner shaft to cut the length of suture.

* * * * *